United States Patent [19]

Pruitt

[11] Patent Number: 5,238,834
[45] Date of Patent: Aug. 24, 1993

[54] CDNA CLONING VECTORS

[75] Inventor: Steven C. Pruitt, Williamsville, N.Y.

[73] Assignee: Health Research, Inc., Buffalo, N.Y.

[21] Appl. No.: 890,355

[22] Filed: May 22, 1992

Related U.S. Application Data

[63] Continuation of Ser. No. 206,426, Jun. 14, 1988, abandoned.

[51] Int. Cl.$^5$ .................... C12N 15/10; C12N 15/66; C12N 15/70; C12N 15/85
[52] U.S. Cl. .................... 435/172.3; 435/240.2; 435/252.3; 435/252.33; 435/320.1
[58] Field of Search ............... 435/320.1, 172.3, 240.2, 435/252.33, 252.3

[56] References Cited

FOREIGN PATENT DOCUMENTS 0092388 10/1983 European Pat. Off. .
0153154  8/1985 European Pat. Off. .
0218468  4/1987 European Pat. Off. .

OTHER PUBLICATIONS

Helfman et al., Methods in Enzyniology, vol. 152, pp. 349-359 (1987).
Deiniyer, Methods in Enzyniology, vol. 152, pp. 371-389 (1987).
Kowalski et al., Gene 35: 45-54 (1985).
Zagursky et al., Methods in Enzyniology, vol. 155, Academic Press pp. 139-155 (1987).
Mead et al., Nucl. Acids Res. 13: 1103-1118 (1985).
Dewte et al., Nucl. Acids. Res. 11:1645-1655 (1983).
Mol. Cell. Biol. 2:161-170, 1982. Okayama, H., and P. Berg. High-efficiency clonging of full length cDNA.
Gene 44:347-351, 1986, Nakamura, K., et al., An improved *Escherichia coli* expression vector for the construction and identification of full-length cDNA clones. *Molecular and Cellular Biology*, vol. 3, No. 2, Feb. 1983 (Washington, D.C.) H. Okayama et al., "A cDNA Cloning Vector That Permits Expression of cDNA Inserts in Mammalian Cells", pp. 280-289.
*Virology*, vol. 139, No. 1, Nov. 1984 (New York) J. C. Carrington et al., "Complementary DNA Cloning and Analysis of Carnation Möttle Virus RNA", pp. 22-31.
*Virology*, vol. 114, No. 2, Oct. 30, 1981 (New York) G. P. Dotto et al., "Functional Analysis of Bacteriophage f1 Intergenic Region", pp. 463-473.
DNA 4; 401-408, 1985, Edwards, D. R., et al., A pBR322-derived vector for cloning blunt-ended cDNA: its use to detect molecular clones or low-abundance mRNA's.
Gene 34:305-314, 1985. Coleclough, C., et al., Use of primer-restriction-end adapters in a novel cDNA cloning strategy.

*Primary Examiner*—Richard A. Schwartz
*Assistant Examiner*—Philip W. Carter
*Attorney, Agent, or Firm*—Scully, Scott, Murphy & Presser

[57] ABSTRACT

The present invention is directed to recombinant DNA vector molecules and uses therefor. More particularly, the present invention relates to the construction of recombinant vectors useful in the high frequency cloning of cDNA. The present invention also relates to vectors capable of directing the synthesis of single stranded cDNA and thereby permitting enrichment of specific sequences by hybridization/selection.

19 Claims, 7 Drawing Sheets

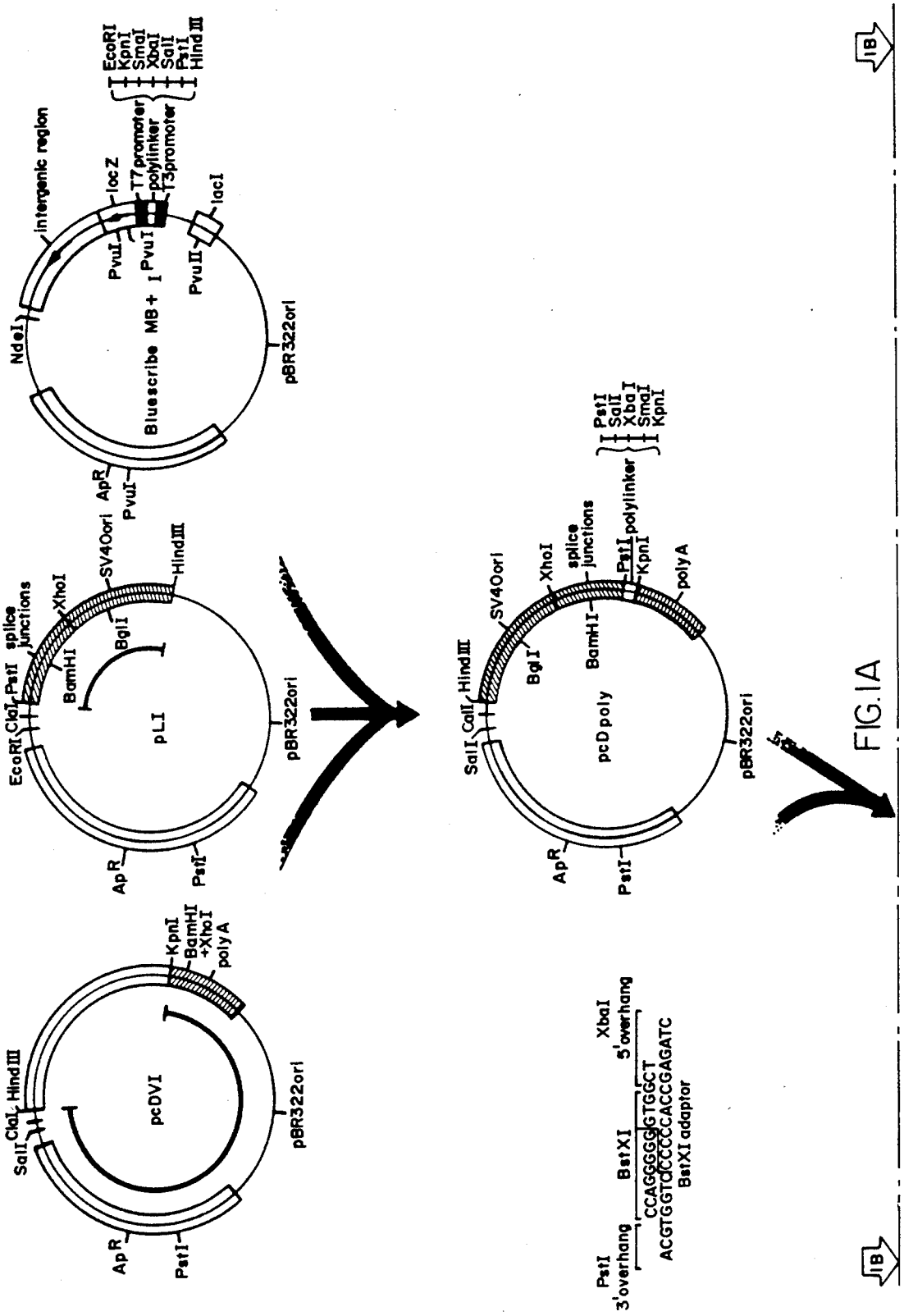
FIG. IA

CDNA CLONING VECTORS

This is a continuation of copending application Ser. No. 206,426, filed on Jun. 14, 1988, now abandoned.

FIELD OF THE INVENTION

The present invention is directed to recombinant DNA vector molecules and uses therefor. More particularly, the present invention relates to the construction of recombinant vectors useful in the high frequency cloning of cDNA. The present invention also relates to vectors capable of directing the synthesis of single stranded cDNA and thereby permitting enrichment of specific sequences by hybridization/selection.

BACKGROUND OF THE INVENTION

Techniques applicable to the generation of complementary DNA (cDNA) to specific messenger RNA (mRNA) provide an important mechanism by which the structure, organization and expression of genetic material in eukaryotic cells can be analyzed. More particularly, the mechanism enables the identification isolation and characterization of specific genes resident in chromosomal DNA. One generalized method by which cDNA can be synthesized is the contacting of a heterogenous mixture of mRNA to reverse transcriptase to generate cDNA:mRNA hybrid molecules. The RNA strands are removed from the hybrids by heat denaturation or by RNase H treatment and the second cDNA strand is synthesized using DNA polymerase (Klenow fragment) and S1 nuclease treatment. The resulting hetergeneous mixture of double stranded cDNA molecules can then be cloned using a variety of techniques into recombinant DNA vector molecules.

In an alternative approach, mRNA molecules are first annealed to vector DNA. Okayama and Berg I (Mol. Cell. Biol 2: 161-170, 1982), and incorporated herein by reference, have described such a strategy for cloning full length, or nearly full length, cDNA molecules in Escherichia coli. This cloning strategy is predicated on linking an oligo (dT) primer to a linearized vector to generate a vector primer and the annealing poly (A)+ mRNA to the oligo (dT) primer. A cDNA strand is synthesized complementary to the annealed mRNA template and the strand terminated with an oligo (dC) linker. The resulting linear molecule is cleaved with the restriction endonuclease Hind III to yield a molecule unable to circularize either by annealing or by ligation due to the presence of incompatible ends. Consequently, circularization is accomplished by the intermolecular ligation of a linker DNA segment comprising a Hind III generated terminus and a oligo (dG) tailed terminus which allows the abridgement of the vector primer Hind III terminus with the oligo (dC) terminated cDNA:mRNA. In this procedure, the RNA strand is replaced by DNA following treatment with RNase H, DNA polymerase and DNA ligase. Okayama and Berg II (Mol. Cell. Biol. 3: 280-289, 1983), and incorporated herein by reference, subsequently described a cloning vector system based on the aforementioned cloning strategy that permits expression of cDNA in mammalian cells. This vector system comprises pcDV1, a recombinant molecule containing a DNA sequence from pBR322 and two segments from Simian Virus 40 (SV40) including the poly A region. Using this system, pcDV1 is restricted with the enzyme Kpn 1 and ligated to an oligo (dT) linker to generate the vector primer. mRNA is then annealed and the cDNA synthesized as described above. The oligo (dC) tailed linker segment required for re-circularization and which contains the SV40 origin of replication, is derived from plasmio pL1. The recombinant cDNA molecule is thus capable of replication in both E. coli and SV40-sensitive mammalian cells.

By employing the general principles of the Okayama and Berg procedure, alternative strategies for cDNA cloning have been developed. Nakamura, et al. (Gene, 44:347-351, 1986) developed an expression vector useful in immunological screening of desired recombinant molecules. In this system, expression of cloned cDNA is directed by tandem lac control regions derived from pUC8 and pUC19. Carrington and Morris (Virology 139: 22-32, 1984) cloned a portion of the Carnation Mottle virus germ using DNA fragments derived from pVC8 and pBR322 instead of the pBR322-SV40 hybrid plasmid described by Okayama and Berg. In another procedure, Coleclough and Erlitz (Gene 34:305-314, 1985) described the use of primer-restriction-end (PRE) adapters in a cDNA cloning strategy. In this procedure, cDNA is synthesized using a PRE adapter as a primer oligonucleotide. One end of the cDNA strand is annealed to a vector by oligo (dC) and (dG) pairing. The other end is ligated by the addition of another PRE adapter.

Although the high efficiency of incorporation of full length cDNA obtained using the Okayama and Berg protocol is a substantial advantage, this protocol has not been employed in many studies due to the relatively low efficiency with which transformants are obtained per microgram of starting vector and polyadenylated RNA, relative to the use of bacteriophage vectors and the difficulties associated with screening bacterial colonies, relative to bacteriophage plaques, using hybridization probes. The present invention describes recombinant DNA vector molecules which allow the efficient cloning of full length cDNA using a modification or the method of Okayama and Berg. The vectors described herein are also useful in the enrichment of specific sequences directly from cDNA libraries by hybridization/selection.

SUMMARY OF THE INVENTION

The present invention is directed to recombinant DNA molecules capable of replication in prokaryotic hosts, and optionally eukaryotic hosts, useful in the high frequency cloning of double-stranded cDNA and in the generation of single stranded cDNA therefrom.

More particularly, one aspect of the present invention relates to recombinant DNA molecules comprising:
(a) a prokaryotic origin of replication;
(b) a selectable marker;
(c) a deoxyribonucleic acid sequence permitting synthesis of said recombinant DNA molecule in a single-stranded form; and
(d) a unique restriction endonuclease site permitting i) a re-circularization of the linear form of said recombinant DNA molecule containing cDNA by intramolecular ligation; and ii) priming of second strand cDNA synthesis.

Even more particularly, the recombinant DNA molecules contemplated by the present invention comprise:
(a) a prokaryotic origin of replication derived from pBR322;
(b) an ampicillin resistance encoding gene;
(c) the intergenic region of bacteriophage F1; and, (d) a unique Bst X1 restriction endonuclease site.

Another aspect of the present invention relates to said recombinant DNA molecules further comprising a eukaryotic origin of replication and a eukaryotic promoter.

Still another aspect of the present invention relates to the use of the intergenic region of bacteriophage F1 in said recombinant DNA molecules to generates single-stranded DNA molecules hereof and which are utilized in nucleic acid hybridization/selection.

The following terms are used in the specification and claims:

| | |
|---|---|
| Annealing: | To hybridize nucleic acid molecules by pairing of A-T or G-C, e.g., an oligo (dG) tail annealing to an oligo (dC) tail. |
| cDNA: | Complementary DNA. DNA which is complementary to a specific sequence of mRNA. |
| Hybridization: | The formation of stable duplexes between complementary nucleotide sequences via base pairing (A-T, G-C). DNA-DNA, DNA-RNA or RNA-RNA hybrids can be formed. |
| Inter-, Intra-molecular ligation: | Circularization of a linear DNA molecule by ligation of two ends is referred to as an intra-molecular ligation. Inter-molecular ligation refers to circularization by abridging the two ends with a second segment of DNA. |
| mRNA: | Messenger RNA. |
| Oligo (dC): | Short length of deoxycytidine molecules which can be added to the 3' end of DNA. |
| Oligo (dG): | Short length of deoxyguanosine molecules which can be added to the 3' end of DNA. |
| Oligo (dT): | Short length of deoxythymidine molecules which can be added to the 3' end of DNA. |
| Poly (A)$^+$: | The tail of adenylic acid residues which is added to the 3' end of many eukaryotic mRNA molecules following transcription |
| Restriction endonuclease digestion: | Cleavage of double stranded DNA by a specific enzyme which recognizes a specific sequence of nucleotide bases. |
| Vector, plasmid, recombinant DNA molecule: | DNA molecules in which non-contiguous sequences have been placed next to each other by in vitro manipulations. In general, the term applies to a DNA molecule, usually derived from a plasmid or bacteriophage, into which fragments of DNA may be inserted or cloned. A plasmid vector replicates autonomously in the cell. An expression vector is one in which fragments of DNA to be inserted are placed "downstream" of a promoter and, hence, their coding sequence is transcribed and translated. |
| Library: | A collection of recombinant DNA molecules carrying DNA inserts from the genome of an organism. As used herein, the libraries comprise cDNA inserts. |

DETAILED DESCRIPTION OF THE INVENTION

Figure 1B:
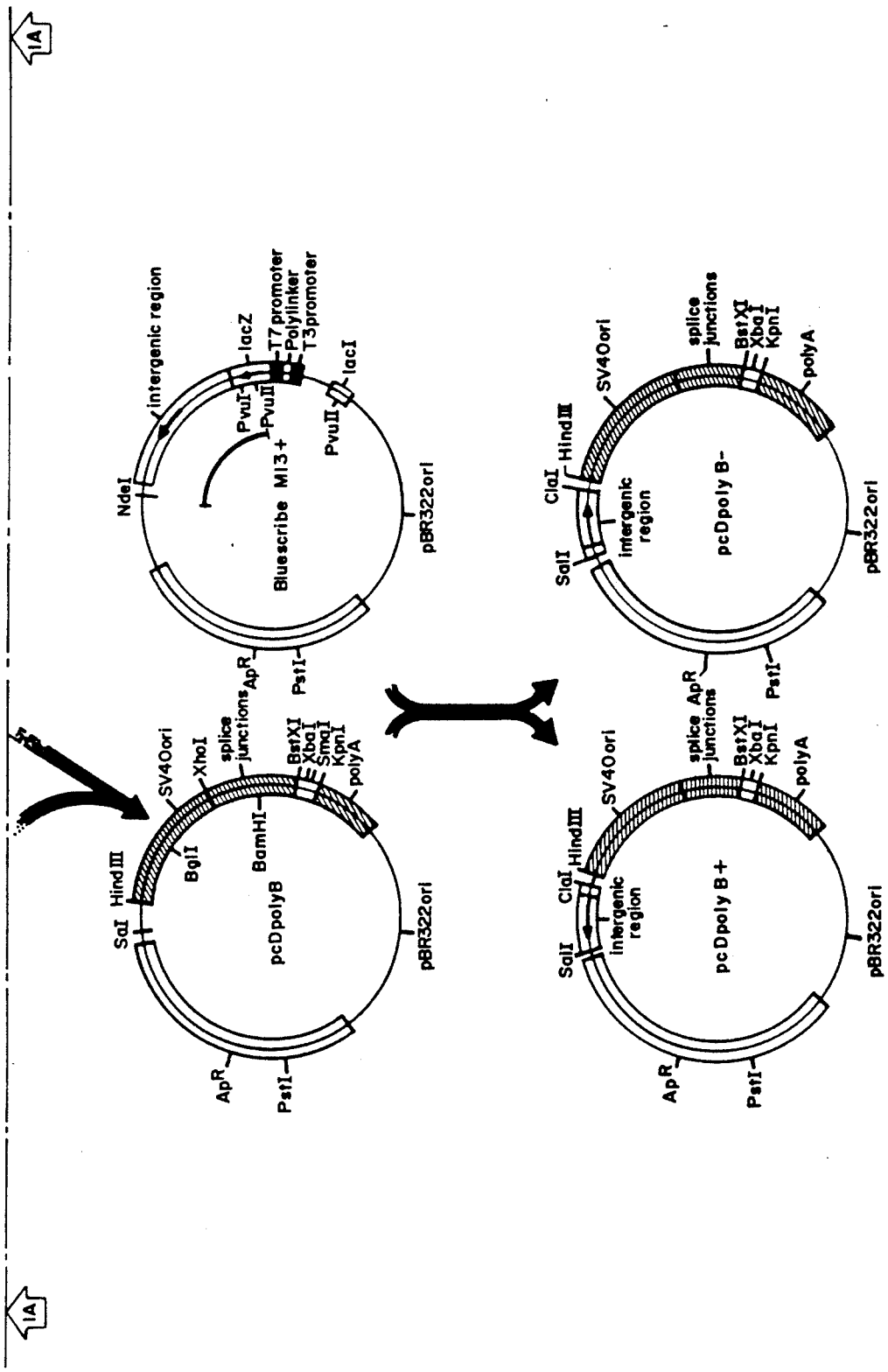
FIG. 1 is a diagrammatic representation depicting the construction of pcDpoly B+ and pcDpoly B—.

The present invention is directed to recombinant DNA molecules capable of replication in prokaryotic hosts, and optionally, in eukaryotic hosts, useful in the high frequency cloning of double-stranded cDNA and in the generation of single-stranded cDNA therefrom. The recombinant molecules contemplated herein comprise a prokaryotic selectable marker (e.g., resistance to an antibiotic) a prokaryotic origin of replication (e.g., ColE1 replication system of pBR322), the intergenic region bacteriophage F1, and a unique restriction site (e.g., Bst X1) permitting an intramolecular ligation following the synthesis of at least one cDNA strand. These recombinant molecules optionally comprise a eukaryotic origin of replication (e.g., from SV40) and eukaryotic regulatory signal sequences (e.g., poly A, splice and early promoter sequences). As used in the specification and claims herein, a recombinant molecules has the same meaning as a plasmid and a vector and is defined to include circular DNA molecules capable of autonomous replication relative to chromosomal DNA in prokaryotic hosts and optionally in eukaryotic hosts. One skilled in the art will immediately recognize that the recombinant molecules considered herein can be varied with respect to origins of replication, selectable markers and unique restriction sites. The subject recombinant molecules are described using components, which, up to the present time, represent the best mode of performing the subject invention. This is done with the understanding that all such variations as will be apparent to the artisan are encompassed by the present invention. Additionally, selectable markers as used herein, refer to the marker and to the nucleic acid encoding said marker. Selectable markers contemplated by the present invention include resistance to antibiotics such as ampicillin, tetracycline, chloramphenicol, kanamycin, neomycin, rifampicin, carbenicillin, streptomycin and the like. Said selectable markers also encompass resistance to phage infection, sensitivity to streptomycin and enzymes which effect colorometric changes. The subject invention is described using ampicillin as the selectable marker which, up to the present time, represents the best marker available. This is done with the understanding that all such selectable markers are encompassed by the present invention.

Okayama and Berg, I and II, supra, have described a strategy for cloning cDNAs in E. coli which yields full length, or nearly full length, cDNA. Although the high efficiency of incorporation of full length cDNA obtained using the Okayama and Berg protocol, is a substantial advantage, this protocol has not been employed in many studies due to the relatively low efficiency with which transformants are obtained per ug of starting vector and polyadenylated RNA, relative to the use of bacteriophage vectors and the difficulties associated with screening bacterial colonies, relative to bacteriophage plaques, using hybridization probes. Two modifications in the original Okayama and Berg method are described herein which overcome these problems. First, to improve the efficiency of synthesis of transformation competent cDNA-vector molecules, the Okayama and Berg method has been modified where the important difference is that the original method requires an intermolecular ligation step to recircularize cDNA containing plasmids and prime second strand cDNA synthesis whereas the scheme described here takes advantage of a Bst X1 site to create a 3' oligo (dG) protruding end and thereby allowing the same steps to be accomplished via an intra-molecular ligation (See FIG. 1). Second, the plasmids described herein are recoverable in the form of circular single stranded DNA due to the presence of the intergenic region of bacteriophage F1. Dotto, et al. (*Virology* 114: 463–473, 198; *J. Mol. Biol.* 153: 169–176, 1981) first observed that insertion of the intergenic region of the phage F1 genome, which contains all of the cis acting elements required for DNA replication and morphogenesis, into the Eco R1 site of pBR322 allowed the packaging and excretion into the culture medium of the pBR322 DNA on superinfection with F1 phage. Additionally, the size of the plasmids which carry the F1 intergenic region is not limited (Dente, et. al. *Nuc. Acid. Res.* 11: 1645–1655, 1983). The presence of the F1 phage intergenic region in the cDNA cloning vectors described herein allows the recovery of cDNA libraries constructed in these vectors in the form of circular single stranded DNA which are then enriched for specific sequences by hybridization/selection. The selected circular cDNA is then utilized to transform a suitable bacterial host, facilitating the isolation of specific cDNA. The modifications described herein maintain the advantage of the original Okayama and Berg procedure in cloning full length cDNA with high efficiency and facilitate use of the procedure for a number of applications.

Construction of the vectors pcDpoly B— and BSB+ enhances the efficiency with which cDNA is incorporated into libraries compared to the method of Okayama and Berg I and II, supra. In the original latter method, a plasmid (either pBR322-SV40 [0.11–0.86] or pcDV1) is opened at the Kpn 1 site and oligo (dT) tailed. The oligo (dT) tail distal to the site at which the RNA will be hybridized is removed by restriction digestion with a second enzyme and the vector fragment is isolated. Polyadenylated RNA is then hybridized to the remaining oligo (dT) tail of the plasmid and copied using reverse transcriptase. An oligo (dC) tail is then added to the 3' end of the cDNA using terminal deoxynucleotidyl transferase and the plasmid is digested with the restriction endonuclease Hind III. The resulting molecule can then be recircularized by ligation to a second DNA fragment, isolated from a second plasmid (either pBR32-SV40 [0.19–0.32] or pL1), which has been prepared such that it contains a Hind III cohesive protruding end on one terminus of the molecule and an oligo (dG) tail on the other. Hybridization of the oligo (dG) tail from the second fragment to the oligo (dC) synthesis which is accomplished using RNase H and DNA polymerase 1. A significant improvement over the Okayama and Berg method and described here (FIG. 2) is that, once the first strand of the cDNA is synthesized and oligo (dC) tailed, the oligo (dG) tail required for priming second strand cDNA synthesis and recircularization of the plasmid is provided by digestion of the plasmid with the restriction enzyme Bst X1. The recognition sequence for Bst X1 is CCANNNNN'NTGG, wherein the plasmids pcDpoly B+, pcDpoly B—, BSB+, and BSB— (See Example 2) the sequence is CAAGGGGG'GTTG. Digestion of each of these plasmids with Bst X1 then results in a $(dG)_4 3'$ protruding end which can be utilized to recircularize the plasmid and to prime second strand cDNA synthesis when hybridized to the oligo (dC) tail present on the cDNA. One of the main advantages of this approach is that, unlike the original Okayama and Berg method which requires an intermolecular ligation for recircularization, the vectors of the subject invention are recirculated by an intramolecular ligation between the oligo (dC) tail of the cDNA and the oligo $(dG)_4$ tail provided by Bst X1 digestion. In addition to simplifying the steps required for construction of cDNA libraries, this difference enhances the efficiency with which circular plasmids competent for transformation are generated.

The efficiency with which full length cDNA is incorporated into cDNA libraries using the original Okayama and Berg procedure has been studied for several sequences including alpha- and beta-globin and HPRT. The frequency of full-length cDNA clones, relative to the total number of clones containing a portion of these sequences, has been estimated to range between 5%, in the case of HPRT, to 10% in the case of the globins. Additionally, in the case of the globins the frequency with which cDNA containing the entire region are generated is at least 30–50%. The high frequency of incorporation of full-length cDNA in libraries constructed using the Okayama and Berg protocol has been attributed to: (1) the use of the vector itself as the primer for both first and second strand cDNA synthesis, 2) the lack of a requirement for treatment of the completed DNA with nucleases prior to insertion into the vector, and 3) the low efficiency with which terminal deoxynucleotidyl transferase utilizes the recessed 3' ends which would result from incomplete first strand synthesis.

The use of the Bst X1 site present in each of the vectors pcDpoly B+, pcDpoly B—, BSB+ and BSB— to generate an oligo (dG) 3' protruding ends for use in recircularization of the cDNA containing plasmids by intramolecular ligation and priming second strand cDNA synthesis as described herein is designed to maintain the features of the Okayama and Berg procedure which lead to a high frequency of incorporation of full-length cDNA. To determine the efficiency with which near full-length cDNA are incorporated into libraries constructed using the Bst X1 cloning procedure, the lengths of cDNA containing two specific sequences, HPRT and alpha-fetoprotein are estimated by digestion of library DNA with a restriction endonuclease, electrophoresis on an agarose gel and detection of either HPRT or alpha-fetoprotein sequences by hybridization to $^{32}p$ labeled probes. The length of the HPRT message is 1.55 kbp including 3' poly-adenylation. Additionally, a cDNA containing full length HPRT coding sequence has been isolated using the Okayama and Berg technique and is 1.35 kbp long, in reasonable agreement with the length of the 1.55 kb polyadenylated mRNA. At least half of the cDNA homologous to the HPRT probe detected in library B constructed using the vector BSB+ are 1.35 kbp +/— approximately 50 bp and contain the full-length coding sequence of this message. Similarly, the expected length of the alpha-fetoprotein message as determined in previous studies is 2.2 kbp and again, over half of the cDNA homologous to the alpha-fetoprotein probe, present in a second library which is constructed using the vector pcDpoly B—, is migrated at the position expected for full length cDNA. Accordingly, the Bst X1 cloning procedure yields a high efficiency of incorporation of full length cDNA.

The synthesis of circular cDNA containing plasmids, which are competent for transformation, by the Okayama and Berg procedure requires an intermolecular ligation step in which an oligo dC tailed cDNA present on one end of a plasmid is joined to a Hind III protruding end on the distal terminus of the plasmid using a bridging fragment which contains an oligo dG tail on one end and a Hind III protruding end on the other. The efficiency which which this step occurs is influenced by both the ratio between the cDNA containing plasmid and the bridging fragment as well as the concentration of the two DNA molecules. The reaction is further complicated by the presence of the DNA fragment containing and Hind III protruding end and an oligo dC tail which results from digestion of the oligo dC tailed cDNA-vector plasmid with Hind III. To increase the efficiency with which cDNA containing plasmids are circularized, a Bst X1 site is incorporated into each of the cloning vectors described herein. The recognition sequence for Bst X1 is CCANNNNN'NTGG, where the sequence utilized here is CCAGGGGG'GTGG. Digestion of this sequence with Bst X1 created a 3' $(dG)_4$ protruding end which substitutes for the bridging fragment required in the Okayama and Berg protocol. This modification eliminates the need for an intermolecular ligation since recircularization of the plasmid can now be accomplished by an intramolecular ligation between the oligo (dC) tailed cDNA and the oligo $(dG)_4$ tail created by Bst X1 digestion. This modification results in a higher ligation efficiency and consequently more efficient incorporation of cDNA-plasmids into libraries. The number of independent transformants/ug of DNA obtained using the Bst X1 method in accordance with the subject invention ranged from about 2.0 to about $8.1 \times 10^6$ which the Okayama and Berg protocol yields between 0.5 and $2.0 \times 10^6$ independent transformants/ug. As described herein the efficiency of transformation of supercoiled pBR322 DNA is approximately $8.0 \times 10^7$/ug, thus as many as 1/10 of the cDNA plasmid molecules generated using the Bst X1 protocol of the present invention are competent for transformation.

With respect to the foregoing, the incorporation of a Bst X1 site is, up to the present time, most useful in practicing the subject invention. The skilled artisan will recognize that many restriction sites may be alternatively incorporated provided that said sites are unique to the vector. All such sites are accordingly encompassed within the scope of the present invention. The scope of the present invention also encompasses recombinant DNA molecules having the identifying characteristics of BSB+, BSB—, pcDpoly B+ and pcDpoly B— and which individually further comprise a first cDNA strand, and optionally, a second cDNA strand. When said recombinant DNA molecules contain SV40-derived DNA, said molecules are capable of expressing cDNA by virtue of the early promoter contained therein.

The present invention also relates to a process for enriching a cDNA library in a first recombinant DNA molecule for specific nucleic acid sequences comprising annealing single-stranded forms of cDNA containing said first recombinant DNA molecules to single-stranded forms of a second recombinant DNA molecule containing the nucleic acid sequence to be enriched with the proviso that the first and second recombinant DNA molecules have the intergenic region from bacteriophage F1 inserted in opposite orientations relative to each other. As defined herein, a cDNA library refers to cDNA ligated into the recombinant DNA molecules BSB+, BSB—, pcDpoly B+ or pcDpoly B—. Accordingly, the first and second recombinant DNA molecules are respectively selected from the group consisting of pcDpoly B— and BSB+, pcDpoly B+ and BSB—, BSB— and pcDpoly B+, BSB+ and pcDpoly B—. More particularly, specific cDNA sequences are isolated from libraries constructed in each of the vectors BSB+ or BSB— and pcDpoly B+ or pcDpoly B— by hybridization/selection. This is possible since the presence of the intergenic region from the bacteriophage F1 allows these plasmids to be encapsulated and isolated as single-stranded circular molecules on super-infection with phage F1 or its derivatives. The single stranded circular DNA is utilized in nucleic acid hybridization reactions and remains competent for subsequent transformation into bacteria. In this study, by way of example, the isolation of HPRT containing cDNA from a library constructed in pcDpoly B— is demonstrated. Two rounds of hybridization selection are utilized and over half of the cDNA present in the second round sublibrary contain the HPRT gene. Additionally, all of the major species which are present in the original library are represented in the sublibraries.

There are a variety of applications for which the recovery of specific cDNA sequences by hybridization/selection is useful. First, identification of a specific cDNA sequence using a purified homologous probe, as demonstrated for HPRT herein, is greatly simplified and is accomplished much more rapidly than is possible using bacteriophage vectors and plaque hybridization techniques. An entire library of $2 \times 10^6$ or more independently derived cDNA sequences is screened using about 50 ul hybridization reactions and a sublibrary containing all of the cDNA homologous to a given probe which are present in the original library is accomplished in less than a week. The most complete cDNA which is present is then selected from the sublibrary directly by size selecting the DNA. The ability to physically separate cDNA containing clones which are homologous to a specific sequence of DNA is valuable in indentifying the individual members of related families of genes since sublibraries of cDNA can be prepared by performing the hybridization step at varying stringencies.

Another significant advantage of the present invention is the ability to select specific cDNA sequences from a cDNA library in the purification of cDNA which is specific to particular cell types or growth stages. It is known that by inverting the orientation of the insertions present in two different cDNA libraries constructed in phagemid vectors it is possible to obtain single stranded DNA in which the opposite strands of sequences common to the two libraries are synthesized and will hybridize while the same strand of the vector from each library is synthesized and consequently does not anneal. Two different cDNA libraries constructed in either the vectors pcDpoly B+ and BSB+ or pcDpoly B— and BSB— are utilized for subtraction of sequences common to the libraries by hybridization selection since the inserts in each of these vector pairs are oriented oppositely. If the single stranded DNA from one of the two lib aries is bound to a sepharose matrix as demonstrated herein for specific probe sequences, then it is possible to physically isolate sublibraries of sequences which are highly enriched for cDNA sequences present in one of two libraries. This approach facilitates isolation of sequences specific to particular cell types since, although current technologies using +/− screening techniques are capable of the isolation of a sample of the messages specific to a particular cell type, the necessity to carry each individual sequence identified through multiple rounds of purification limits the number of sequences which are identified using bacteriophage vectors to a relatively small number. Using the vectors described herein, it is now possible to create sublibraries of sequences which contain many or most of the messages specific to particular cell types by hybridization selection.

cDNA libraries constructed in the expression vectors pcDpoly B+ or pcDpoly B− and which have been enriched for sequences present in a specific cell type greatly facilitate attempts to identify specific cDNA sequences on the basis of the function they express in mammalian cells. A previous attempt to identify a plasmid containing the HPRT sequence from a cDNA library constructed in the vector pcDV was not successful (Okayama and Berg, II, supra). The HPRT sequence is present in the library used in that study at a frequency of approximately $2 \times 10^5$ and, when isolated by colony hybridization techniques and transfected into HPRT deficient cells as a purified plasmid, conferred resistance to HAT media. However, mixing experiments demonstrated that HPRT+ cells are obtained only if the HPRT containing cDNA is present at a frequency of greater than $1 \times 10^{-3}$ to $1 \times 10^{-4}$. To obtain this frequency, in the case of the HPRT gene, it is necessary to enrich for this sequence by a factor of approximately 100 over the concentration in the original cDNA library. By construction of cDNA libraries in one of the pcDpoly B vectors from cells which express a cDNA such as HPRT, for which a function can be assayed and enrichment of this library by subtractive hybridization/selection using a second library constructed in one of the BSB vectors from cells which do not express the function (in this case an HPRT− deletion mutant), it is possible to obtain sublibraries which are sufficiently enriched to isolate even relatively rare sequences on the basis functional assays. This approach is applicable to any situation where closely related cell types which differ in their expression of a given gene product can be identified.

A deposit of a biologically pure culture of the following strains was made with the American Type Culture Collection (ATCC), 12301 Parklawn Drive, Rockville, Md. on Jun. 9, 1988 and accession numbers indicated were accorded after successful viability testing and the requisite fees were paid. Access to said culture will be available during pendency of the patent application to one determined by the Commissioner to be entitled thereto under 37 C.F.R. §1.14 and 35 U.S.C. §122. All restriction on availability of said culture to the public will be irrevocably removed upon the granting of a patent based upon the application and said culture will remain permanently available for a long term of at least five years after the date of deposit. Should the culture become nonviable or be inadvertently destroyed, it will be replaced with a viable culture(s) of the same taxonomic description.

| Strain | ATCC No. |
| --- | --- |
| Plasmid in *Escherichia coli* strain HB101, BSB+ | 67724 |
| Plasmid in *Escherichia coli* strain HB101, BSB− | 67725 |
| Plasmid in *Escherichia coli* strain HB101, pcDpoly B+ | 67726 |
| Plasmid in *Escherichia coli* strain HB101, pcDpoly B− | 67727 |

The following examples further illustrate the present invention.

EXAMPLE 1

Recombinant DNA Procedures

Unless otherwise specified herein, manipulation of recombinant molecules and the preparation of solutions are by standard, known techniques. Such techniques are described in Maniatis, et al. *Molecular Cloning: A Laboratory Manual*, Cold Spring Harbor Laboratory, Cold Spring Harbor, 1982, pp 1-500.

Cell Cultures and Preparation of Polyadenylated RNA

Both F9 (Bernstine, et al., *P.N.A.S.* 70:3899-3903, 1973) and P19S1801A1 (McBurney, et al., Nature 299: 65-167, 1982) cells are cultured in DME supplemented with 10% (v/v) fetal calf serum. To induce differentiation of F9 cells, approximately $10^6$ cells/ml are cultured in bacterial grade petri dishes in the presence of $10^7$ M retinoic acid for 5 days (Hogan, et al., *Nature* 291: 235-237, 1981). Aggregates are collected by centrifugation at $500 \times g$ for 5 minutes and cells are lysed by addition of 100 volumes of a solution containing 4 M guanidine isothiocyanate, 5 mM Na− citrate (pH 7.0), 1 mM beta-mercaptoethanol and 0.5 (v/v) sarkosyl (GITC solution). Three different protocols are used to induce differentiation of OIAI cells as described by McBurney, et al., supra. For induction of aggregates with either retinoic acid or DMSO, a suspension of approximately $10^5$ cells/ml is grown in bacterial grade petri dishes in the presence of either $10^7$ M retinoic acid or 0.4% (w/v) DMSO for 3 days. Cells are then transferred to tissue culture dishes and cultured in the absence of inducer for various times. For induction of monolayers with retinoic acid, cells are plated directly onto tissue culture dishes and cultured in the presence of inducer for 3 days followed by culture in the absence of inducer for various times. To harvest the induced cultures, culture media is removed and 5 ml of GITC solution is added to each dish of cells. RNA is isolated from the homogenates by addition of 1.5 g CsCl/2.5 ml of homogenate and the homogenate is layered over a 1.5 ml cushion of 5.7 M CsCl, 10 mM Tris-HCl (pH 7.5), 1 mM EDTA and centrifuged for 24 hours, at 25,000 rpm in an SW rotor (Maniatis, et al., supra). The RNA pellet is resuspended in 300 ul of 10 mM Tris-HCl (pH 7.5), 1 mM EDTA, 1% (w/v) SDS, and 1 mg/ml protease K, extracted once with phenol and once with 25:1 chloroform:isoamyl alcohol and precipitated by addition of Na-acetate (pH 5.5) to 0.3 M and 2 volumes of ethanol. RNA is resuspended in 100 ul of dH$_2$O containing 1 mM dithiothreitol and 100 units of RNasin (Promega). Polyadenylated RNA is isolated using oligo dT cellulose paper (Amersham) as described by the manufacturer.

Oligo dT Tailing of Vector DNA

Vector DNA are prepared for use by digesting 200 ug with 400 units of Kpn 1 (BRL or NEB) in 400 ul of digestion buffer for 3 hours. DNA is CHCl$_3$—OH extracted, ethanol precipitated and resuspended in 200 ul of 10 mM TRis-HCl, 1 mM EDTA (TE). Approximately 50 ul of 5×terminal deoxynucleotidyl transferase (TdT) reaction buffer (100 mM potassium cacodylate, pH 7.2, 2 mM CoCl$_2$ and 0.2 mM diothiothreitol), TTP to a final concentration of 240 mM and 100 units of TdT (BRL) are added and the reaction incubated at 37° C. for 30 minutes. The reaction is stopped by addition of 10 ul of 0.5 EDTA, extracted twice with CHCl$_3$—OH and DNA precipitated by addition of Na-acetate to 0.3 M and 2 volumes of ethanol. Following resuspension in 200 ul TE and reprecipitation, the DNA is resuspended in 360 ul TE and either 40 ul of 10×Xba 1 digestion buffer and 400 units of Xba 1 (BRL) in the case of pcDpoly B+ or B− (See Example 2) or 40 ul of 10×Bam H1 digestion buffer and 400 units of Bam H1 (BRL) in the case of BSB+ or BSB− (See Example 2) are added, the reaction is incubated at 37° C. for 3 hours and DNA electrophoresed on 1% (w/v) agarose gels. The vector fragment is isolated on DE B1 paper, recovered by elution with 1.0 M NaCl, 10 mM Tris-HCl (pH 7.5) and 1 mM EDTA and precipitated by addition of 2 volumes of ethanol. The pellet is resuspended in 300 ul TE and NaCl is added to a final concentration of 1 M. Oligo dT tailed vector DNA are then purified by binding and elution from an oligo (dA)-cellulose column as described by Okayama and Berg I, supra. The DNA eluted from the column is extracted 1×with CHCl$_3$—OH, ethanol precipitated and resuspended in 50 ul of TE.

Construction of cDNA Libraries

Figure 2:
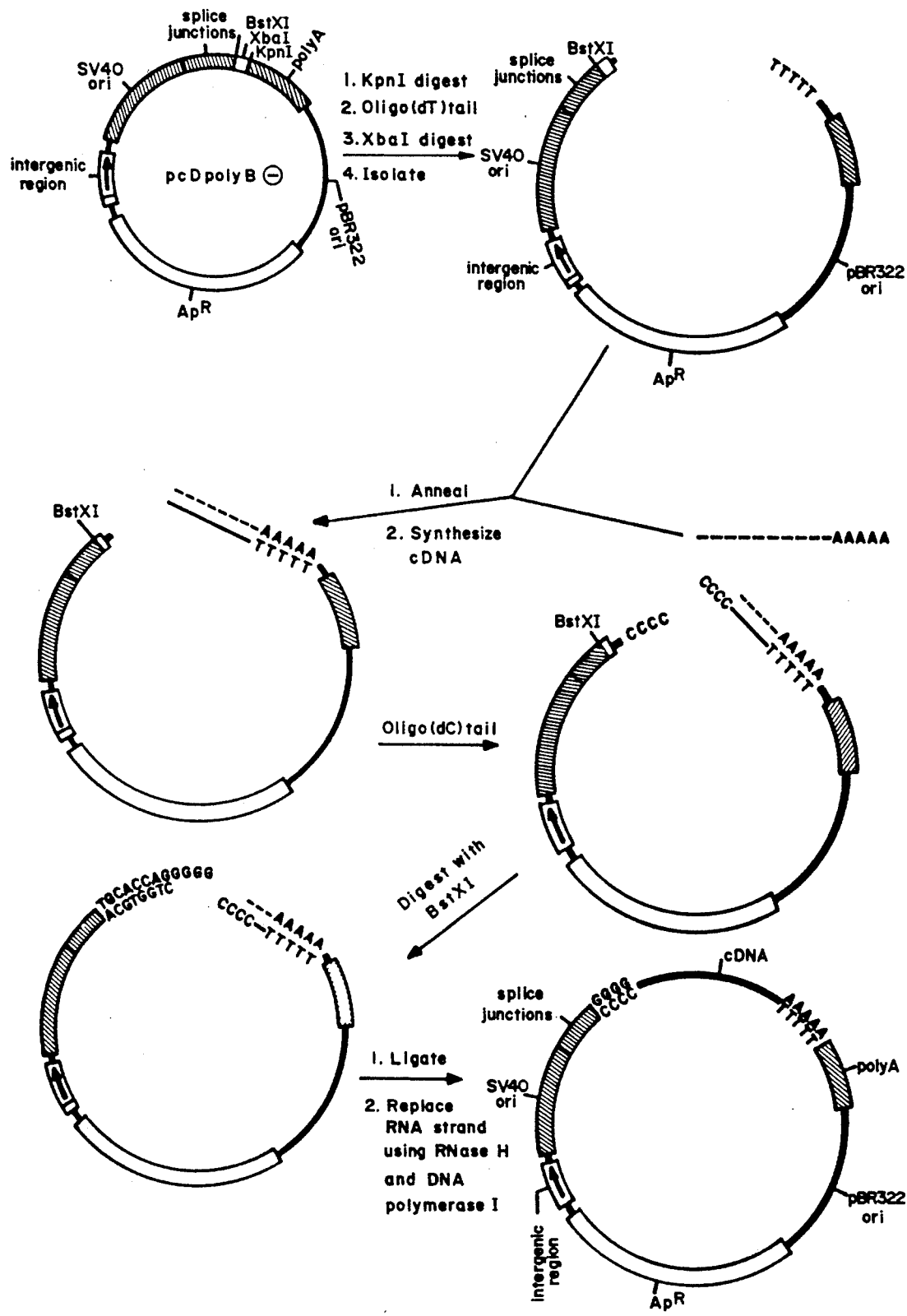
FIG. 2 is a diagrammatic representation depicting the construction of a cDNA clone in pcDpoly B—.

The construction of a cDNA clone is summarized in FIG. 2, exemplified using pcDpoly B−.

Step 1. First Strand cDNA Synthesis

First strand cDNA synthesis was performed essentially as described by Okayama and Berg I, supra, except that the reaction also contained 40 units of RNasin and is performed in a final volume of 20 ul/ug of vector DNA at 42° C. for 60 minutes. The reaction is stopped by addition of 170 ul TE, 5 ul 0.5 M EDTA and 5 ul 10% (w/v) SDS. The solution is extracted once with phenol, once with CHCl$_3$—OH and precipitated by addition of 200 ul NH$_4$Ac and 800 ul of ethanol, incubation at room temperature for 60 minutes and centrifugation. The pellet is washed with 70% (v/v) ethanol, resuspended in 200 ul TE and reprecipitated as before.

Step 2. Oligo (dC) Addition

The pellet containing the vector-cDNA-RNA hybrid is resuspended in 75 ul of TE, 20 ul of 5×TdT buffer, dCTP to a final concentration of 25 uM and 1.5 units of TdT are added and the reaction is incubated at 37° C. for 30 minutes resulting in the addition of approximately 5 to 10 dC residues per end. The reaction is stopped by addition of 5 ul of 0.5 M EDTA and 5 ul of 10% (w/v) SDS, extracted once with CHCl$_3$—OH and precipitated by addition of 110 ul NH$_4$-acetate and 440 ul of ethanol.

Step 3. Bst X1 Digestion

The pellet from the oligo dC tailing step is resuspended in 45 ul of TE, 5 ul of 10×Bst X1 digestion buffer, and 10 units of Bst X1 (NEB) are added. The reaction is incubated at 55° C. for 60 minutes and stopped by extraction with phenol 1×, CHCl$_1$—OH 1× and precipitation with 5 ul of Na-acetate and 120 ul of ethanol.

Step 4. Ligation and Second Strand cDNA Synthesis

The pellet from the Bst X1 digestion step is resuspended in 900 ul of TE and 100 ul of 10×ligation buffer (660 mM Tris-HCl pH 7.6, 66 mM, MgCl$_2$, 100 mM DTT, 1 mM ATP) and 10 units of T4 DNA ligase (BRL) are added. The reaction is incubated overnight at 15° C., transferred to 4° C. and supplemented with 1 ul 10 mM ATP, 1 unit T4 DNA ligase, each of dATP/dCTP/dGTP/TTP to a final concentration of 5 uM, 0.8 units of RNase H (Amersham) and 25 units of DNA polymerase 1 (Amersham). The reaction is then incubated at 12° C. for 60 minutes, 22° C. for 60 minutes and 12° C. for 60 minutes.

Step 5. Transformation and Amplification of cDNA Libraries

The second strand synthesis reaction is divided into 100 ul aliquots and each aliquot is used to transform 400 ul of competent *E. coli* strain MC 1061 cells. Competent cells are prepared by pelleting a culture of MC 1061 cells grown in L-broth to an O.D. 650 nM of 0.6, resuspending the cells in ½ volume of 50 mM CaCl, repelleting, resuspension in 1/25 volume of 50 mM CaCl and incubating at 4° C. for between 2 and 5 hours. Cells prepared in this way routinely gave a transformation efficiency of approximately $8.0 \times 10^7$ transformants/ug of pBR322 DNA. Transformation is performed at 4° C. for 30 minutes followed by 2 minutes at 45° C. and cells are pooled and incubated in 500 ml of Brain Heart Infusion (GIBCO) for 60 minutes at 37° C. Following incubation, aliquots are taken for titering and plated on 1.5% (w/v) agar containing 100 ug/ml ampicillin. Ampicillin is also added to the 500 ml culture to a final concentration of 100 ug/ml. Following incubation at 37° C. for 12 hours, DMSO is added to 10 ml aliquots of the cDNA libraries to a final concentration of 7% (w/v), the aliquots frozen in liquid N$_2$ and stored at −70° C.

To prepare large quantities of double stranded cDNA, a 10 ml aliquot of the frozen library is thawed at 37° C., the cells pelleted by centrifugation at 4,000×g for 5 minutes, resuspended in 5 ml of L-broth, inoculated to 500 ml of Brain Heart Infusion and plasmid preparations performed as described in Maniatis, et al., supra.

Figure 3:
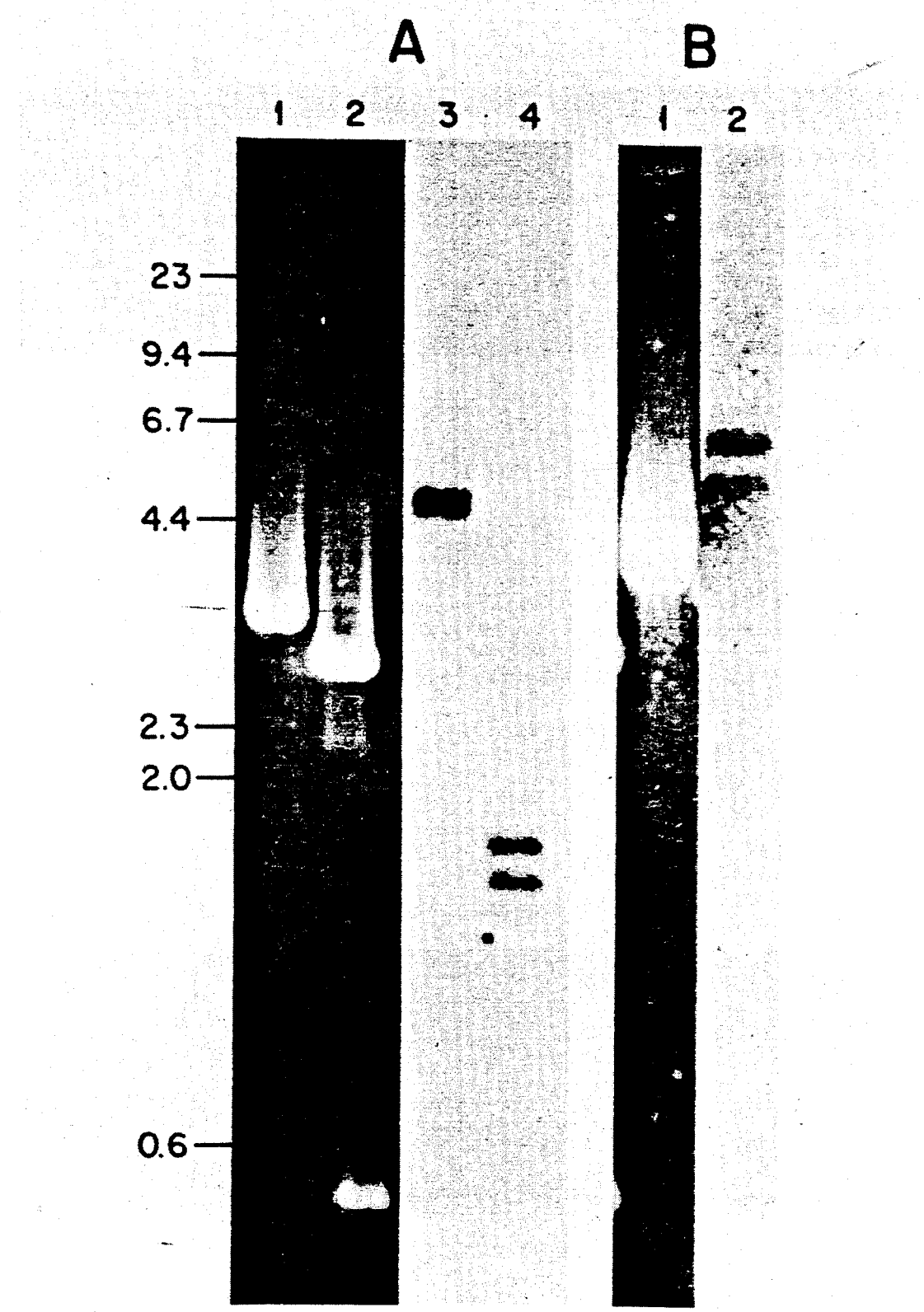
FIG. 3 is a photographic representation showing the efficient incorporation of near full-length HPRT and alpha-fetoprotein cDNA into BSB+ and pcDpoly B— libraries.

The synthesis of a cDNA library is summarized in FIG. 3, exemplified using pcDpoly B−. To construct a cDNA library using the vectors pcDpoly B+, pcDpoly B−, BSB+, or BSB−, the vector DNA is first prepared by digestion with Kpn 1 and an oligo (dT) tail of approximately 60–80 nucleotides is added using terminal deoxynucleotidyl transferase. The unwanted oligo (dT) tail on one end of the vector is removed by digestion with Xba 1 and the tailed vector DNA is purified as described above. Polyadenylated RNA is then hybridized to the remaining oligo (dT) tail and the first strand of the cDNA insert is synthesized using reverse transcriptase. The cDNA is then oligo (dC) tailed using terminal deoxynucleotidyl transferase. To provide an oligo (dG) tail complementary to the oligo (dC) tail present on the cDNA, the vector-RNA-cDNA hybrid is digested with Bst X1. The oligo (dC) and oligo (dG) tails are then annealed and the recircularizated vector is ligated. The RNA strand is removed using RNase H and the plasmid is repaired with DNA polymerase 1.

Transfer of Libraries to *Escherichia coli* Strain 71-18 and Isolation of Single Stranded DNA.

*Escherichia coli* 71-18 cells are made competent for transformation using the protocol described above for MC 1061 cells. Approximately 10 times the number of 71-18 transformants as are present in the original MC 1061 library are generated and 10 ml aliquots of the library are frozen as described above. To prepare single stranded copies of the cDNA present in the library, a 10 ml aliquot of 71-18 cells containing the library is inoculated into 500 ml of brain heart infusion containing 100 ug/ml ampicillin and the culture grown to an O.D. 650 nM of 0.3. The culture is then inoculated with a 5 ml of a saturated culture of bacteriophage VCS257-M13 (Vector Cloning System) in bacterial strain 71-18 and incubated at 37° C. for an additional 12 hours. Cells are removed by centrifuging the culture $2 \times$ for 5 minutes each a $5000 \times g$. The supernatant is brought to a final concentration of 0.3 M NaCl and 3.0% (w/v) polyethylene glycol 8000, incubated at 4° C. for 4-8 hours and centrifuged for 10 minutes at $10,000 \times g$. The pellet is washed with 95% (v/v) ethanol, gently resuspended in 5 ml of TE, extracted once with phenol, once with $CHCl_3$—OH, and the DNA precipitated by addition of Na-acetate to 0.3 M and 2 volumes of ethanol and stored in TE.

Hybridization/Selection

Specific sequences are selected from total single stranded cDNA libraries by hybridization to matrix bound probe sequences. DNA is bound to a cyanogen bromide activated sepharose matrix by procedures described in Arndt-Jovin, et al., *Eur. J. Biochem.* 54: 411-418, 1975. In cases where a specific sequence from a purified plasmid is used as a probe, DNA fragments resulting from restriction endonuclease digestion of CsCl purified plasmids are isolated sequentially from 2-1% (w/v) agarose gels by collection on DE 81 paper and elution in 1 M NaCl, 10 mM Tris-HCl (pH 7.5), 1 mM EDTA. The DNA pellet is washed twice with 70% (v/v) ethanol and resuspended in $dH_2O$ at a concentration of approximately 1 ug/ul. To bind DNA from a cDNA library to sepharose 4B, single, stranded DNA is prepared, precipitated, washed and resuspended in $dH_2O$ as aforementioned described. Cyanogen bromide activated sepharose 4B (Pharmacia) is prepared for binding by washing with an approximately $100 \times$ excess each of 1 mM HCl, $dH_2O$, and 10 mM K-phosphate (pH 8). The DNA is heated in a boiling water bath for 10 minutes and chilled on ice immediately prior to addition to the matrix. The DNA-matrix mixture is incubated at room temperature for 2-18 hours and the matrix washed sequentially with excess $dH_2O$, 0.1 mM Tris-HCl (pH 8.0) +1.0 mM EDTA and incubated for 4 hours at room temperature. Following incubation the matrix is washed sequentially with 10 mM K-phosphate (pH 8.0), 1.0 M K-phosphate (pH 8.0), $dH_2O$ and 10 mM Tris-HCl (pH 7.5)+1 mM EDTA. Use of $^{32}p$ labeled DNA demonstrates that greater than 90% of the DNA is bound under these conditions.

For hybridization of single stranded library DNA to matrix bound DNA, the DNA matrix (25-50 ul for specific probes and 200-500 ul for matrix bound cDNA library probes) is washed 4 times with a 20-50 fold excess of hybridization buffer (250 mM KCl, 10 mM Tris-HCl, pH 8.0, 1 mM EDTA). Between 10 and 100 ug of single stranded cDNA library DNA in $1 \times$ hybridization buffer is added to the matrix, the mixture is overlayed with paraffin oil and incubated at temperatures varying between 50° C. and 58° C. for times ranging between 12 and 48 hours in different experiments.

To recover cDNA hybridizing to the matrix, the matrix is transferred to a 15 ml disposable column and washed with 250-500 ml of $1 \times$ hybridization buffer, at the hybridization temperature, followed by 250-500 ml of $\frac{1}{2} \times$ hybridization buffer at 22° C. The matrix is recovered and 100 ul of TE added. Immediately prior to transformation, the matrix in TE is heated to 80° C. for 10 minutes and chilled on ice. Approximately 500 ul of competent MC 1061 cells are added and the transformation performed as described above, except that incubation at 37° C. in the absence of ampicillin is continued for 2.5 hours and the cells then pelleted and plated on agar containing 100 ug/ml ampicillin. Colonies are collected from the plates by addition of 8-10 ml of L-broth to create enriched sublibraries.

Specific cDNA Libraries

As used in the specification herein, Library 8 refers to a cDNA library constructed using the BSB+ vector. Library 9 refers to a library constructed using pcDpoly B−.

EXAMPLE 2

Construction of Vectors

The construction of vectors pcDpoly B+ and pcDpoly B− is shown in FIG. 1. Plasmid pcDpoly is constructed by a three-way ligation between the Kpn 1 to Hind III fragment of pcDVll (containing the SV40 polyadenylation site and pBR322 sequences; Okayama and Berg (II), supra), the Hind III to Pst 1 fragment of pL1 (containing the SV40 early promoter and splice sites; Okayama and Berg (II), supra) and the Pst 1 to Kpn 1 polylinker fragment from the vector Bluescribe M13+ (Vector Cloning Systems). Plasmid pcDpoly is converted to pcDpoly B by use of a synthetic oligonucleotide with the sequence:

5′CTAGAGCCACCCCCCTGGTGCA3′ to insert a Bst X1 site (i.e., 5′CCAGGGGGGTGG3′) between the Pst 1 and Xba 1 site of the polylinker region of pcDpoly by cleaving the plasmid with Pst 1 and Xba 1, ligating to the oligonucleotide and filling in the resulting gap with the large fragment of DNA polymerase I. Sequence analysis demonstrates that the Xba 1 site is lost at this step due to filling in and blunt end ligation between the 5′ protruding end created by Xba 1 digestion of the plasmid and hybridization of the oligonucleotide to the 3′ protruding end created by Pst 1 digestion. Since a unique restriction endonuclease site located between the Bsy X1 and Kpn 1 sites is required, an Xba 1 linker is inserted at the Sma 1 site located between the Bst X1 and Kpn 1 sites. The resulting plasmid is called pcDpoly B and has the structure shown in FIG. 1. The final step in the construction of pcDpoly B+ and pcDpoly B− is the insertion of Nde 1 to Pvu II fragment from Bluescribe M13+ (containing the bacteriophage F1 intergenic region) between the Sal 1 and Cla 1 sites of pcDpoly B using Sal 1 and Cla 1 linkers. These vectors are capable of expressing cDNA contained therein in eukaryotic cells due to the SV40 early promoter.

Vectors BSB+ and BSB− are constructed from Bluescribe M13+ or Bluescribe M13− by insertion of the aforementioned synthetic oligonucleotide between Pst 1 and Xba 1 sites of the polylinker region as described for the construction of pcDpoly B+ and pcDpoly B−.

EXAMPLE 3

Efficiency of cDNA Library Construction

The vectors described in Example 2 are used to determine the efficiency of cDNA library construction using the methods of Example 1.

Specifically, libraries are constructed using the pcDpoly B− and BSB+ vectors and the efficiency with which independent transformants are obtained is determined. The number of independent transformants obtained per ug of starting vector DNA ranged from about 2.0 to about $8.1 \times 10^6$ and averaged about $3.0 \times 10^6$.

To assay the efficiency with which near full length cDNA are incorporated into libraries produced using the Bst X1 cloning procedure (Example 1), DNA from library B is probed for the presence of cDNA containing sequences homologous to the hypoxanthine guanine phosphoribosyl transferase (HPRT) gene. DNA from +his library is digested with Eco R1, electrophoresed on a 1% (w/v) agarose gel, transferred to nitrocellulose and probed with a $^{32}P$ labeled 250 bp HPRT containing DNA fragment (produced by digestion of the plasmid pMEV with Hind III and nick translation). FIG. 3 (panel A, lane 3) demonstrates that the HPRT probe detects two major bands with lengths of approximately 4.7 and 4.4 kpb. The vector BSB+ is 3.214 kbp in length, thus the HPRT containing inserts are approximately 1.5 and 1.2 kbp in length. To obtain a more accurate estimate of the lengths of the inserts, library 8 (constructed using BSB+) DNA is also digested with Pvu II and probed for HPRT sequences. Pvu II cleavage sites are located at positions 136 bp 5' and 362 bp 3' to the cDNA insertion site in the vector. FIG. 3 (panel A, lane 4) demonstrates that the sequences detected in library B following digestion with Pvu II, by the HPRT probe are 1.75 kpb and 1.55 kbp in length. Thus the lengths of the HPRT containing lengths are more accurately estimated to be 1.35 and 1.15 kbp. Previous studies have demonstrated that the HPRT message from human cells, including the 3' polyadenylation, is approximately 1.55 kb in length (Jolley, et al. P.N.A.S. 80: 477-481, 1983). Additionally, previous isolation of a full length cDNA using the Okayama and Berg I, supra, method yielded an approximately 1350 bp cDNA, in reasonable agreement with the predicated message size (Jolley, et al., supra). This cDNA contained an 85 bp 5' non-translated leader region, a 654 bp coding sequence and a 3' non-coding tail of approximately 600 bp. A 1292 bp mouse cDNA sequence has also been isolated from a library constructed using an S1 nuclease step to blunt end the double stranded cDNA. The coding region in this sequence was 657 bp and is flanked by an 87 bp long 5' leader and a 548 bp long 3' tail. On the basis of these studies it is likely that the larger of the two classes of HPRT containing inserts (approximately 60% present in library B, constructed using the Bst X1 method, contain the full coding sequence and are close to full length copies of the message.

To confirm that efficient incorporation of near to full length cDNA is also obtained using the pcDpoly B− vector, library 9 (constructed using pcDpoly B−) is screened for the presence of cDNA homologous to the message encoding alpha-fetoprotein. The alpha-fetaprotein message is approximately 2.2 kbp in length (Scott, et al., Nature 310: 562-567, 1984) and the vector pcDpoly B− is 3.7 kbp in length, thus a plasmid containing the full length cDNA should be approximately 5.9 kbp. Library 9 DNA is digested with Sal 1 for which there is a single recognition sequence present in the vector and no recognition sequence in the cDNA, electrophoresed on a 1% w/v) agarose gel, transferred to nitrocellulose and probed for alpha-fetoprotein sequences using a 1.1 kbp probe (produced by Eco R1 digestion of the plasmid pAFP2E homologous to the 3' end of the message. FIG. 3 (panel B, lane 2) demonstrates that approximately 60% of the plasmids present in library 9 which contain sequences homologous to this probe are approximately 5.8 kbp in length and are near to full length copies of the alpha-fetoprotein message. A high proportion of near-full length HPRT containing cDNA (25-30%) have also been detected in library 9 (discussed below).

EXAMPLE 4

Enrichment of HPRT Containing cDNA by Hybridization/Selection

Figure 4:
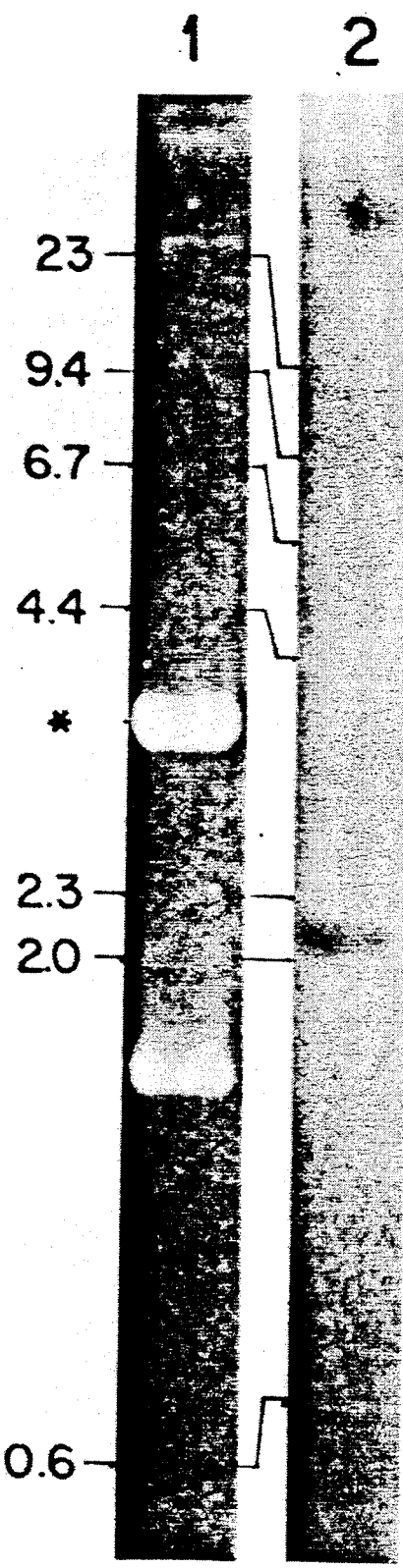
FIG. 4 is a photographic representation showing the isolation of single-stranded circular cDNA library sequences.

To test the efficiency with which a specific cDNA is recovered as a single stranded DNA, library 8 is transferred to E. coli strain 71-18 which exhibits the F phenotype. The library in strain 71-18 is grown to an O.D. 650 mM of 0.3 and superinfected with an approximately 20:1 ratio of the bacteriophage VCSM13 (a derivative of F1, Vector Cloning Systems), the culture is incubated for an additional 8-12 hours and single stranded DNA was isolated, electrophoresed on a 1% (w/v) agarose gel and probed for HPRT sequences using the 250 bp Hind III probe fragment from pMEV described above. FIG. 4, lane 1, shows the single stranded DNA following staining with ethidium bromide and demonstrates that the cDNA containing plasmids are recovered in approximately a 1:1 ratio relative to the helper virus DNA (marked with an asterisk). FIG. 4, lane 2, shows the same DNA following transfer to a nitrocellulose filter hybridization to the HPRT probe and autoradiography. A band migrating slightly larger than the bulk of the cDNA and BSB+ vectors is detected demonstrating the plasmids containing the HPRT sequence are present. Similar results have been obtained for both the HPRT and AFP cDNA present in Library 9.

Figure 5:
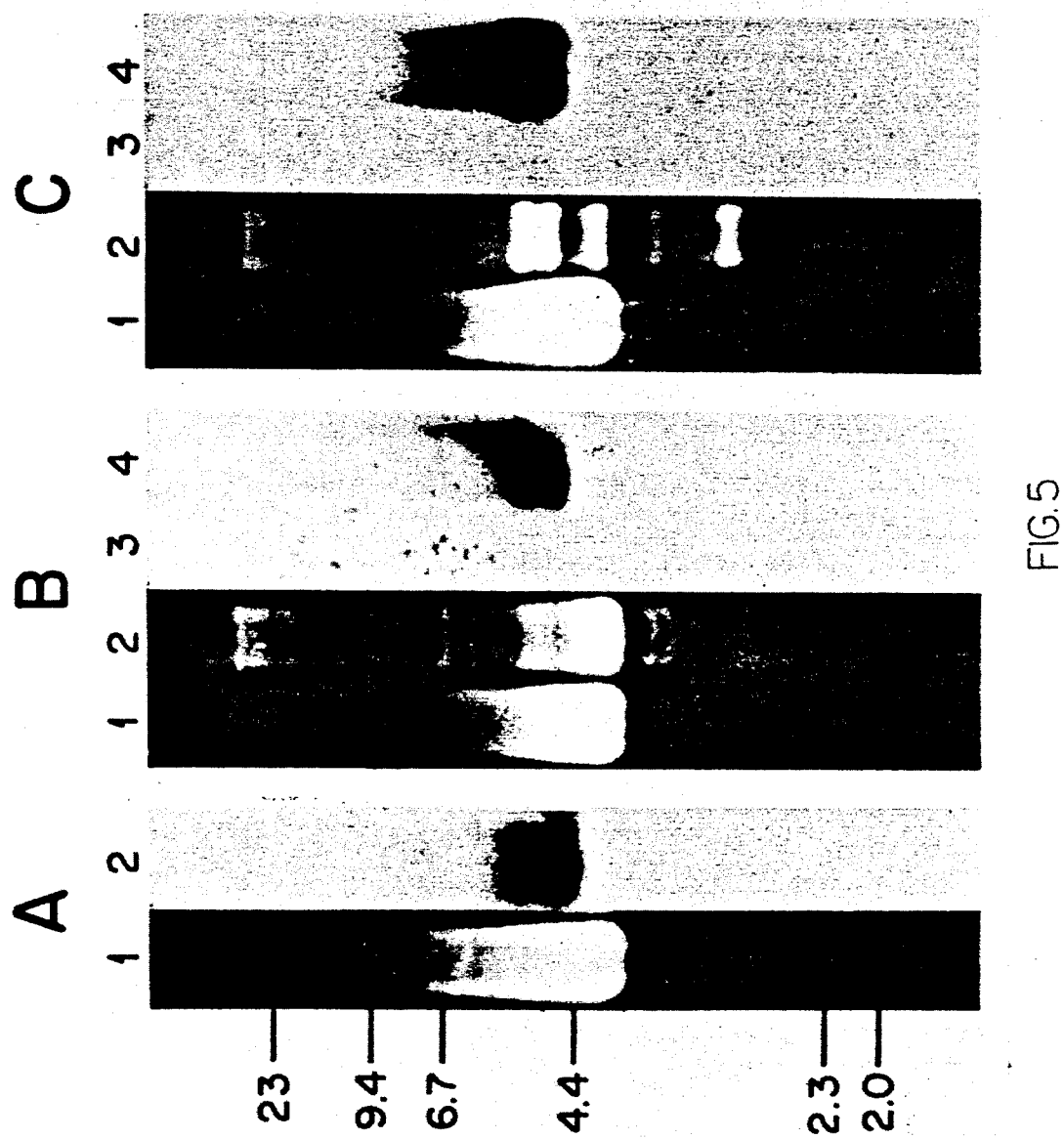
FIG. 5 is a photographic representation of HPRT cDNA clones obtained by hybridization/selection.

To determine if a specific cDNA sequence is recovered efficiently from a single stranded cDNA library, the 250 bp Hind III fragment from the plasmid pMEV is used as a probe to attempt to recover HPRT containing cDNA from Library 9. The probe fragment is denatured and bound to a cyanogen bromide activated sepharose 4B matrix using approximately 10 ug of DNA/50 mg of matrix. The probe-matrix is then washed repeatedly as described in Example 1 and resuspended in hybridization buffer (250 mM KCl, 10 mM TRis-Hcl pH 7.5, 1 mM EDTA). Single stranded Library 9 DNA (50 ug) is then added in hybridization buffer to approximately 25 ul of the probe-matrix such that the final Library 9 DNA concentration is 1 mg/ml in a total volume of 50 ul. The reaction is overlayered with paraffin oil, heated to 80° C. for 5 minutes, and transferred to 55° C. for 18 hours Following hybridization, the matrix is transferred to a 15 ml disposable column and washed with a total volume of 500 ml 1×hybridization buffer at 55° C. followed by 250 ml ½×hybridization buffer at room temperature. The matrix is recovered and resuspended in 100 ul of TE buffer, heated to 80° C. for 10 minutes, transferred to ice and used to transform competent MC 1061 cells. Transformants were grown in the absence of selection for 2.5 hours and plated to agar containing 100 ug/ml ampicillin. Approximately 5,000 clonies are obtained To determine whether HPRT containing cDNA are present in the transformants, the transformants are pooled by addition of L-broth to the plates and the resulting bacterial suspension is cultured for approximately 12 hours at 37° C. A portion of each culture is then utilized to establish a frozen stock and the remainder used to prepare DNA using standard and known miniprep procedures. The isolated DNA is digested with the restriction enzyme Sal 1, which cleaves once in the vector but not in the HPRT sequence and the digested DNA electrophoresed on a 1% (w/v) agarose gel in parallel with 5 ug of the unfractioned Sal 1 digested Library 9 DNA. The results of this assay are shown in FIG. 5, where panel B, lane 1, shows the unselected library DNA and lane 2 shows the HPRT selected DNA after staining the ethidium bromide. To determine if the selected sublibrary contained HPRT cDNA, the DNA is transferred to nitrocellulose and probed with the 250 bp pMEV probe fragment described above. Comparison of panel A, lane 1 (unfractioned Library 9) with panel B, lane 3 (pMEV selected Library 9) of FIG. 5, demonstrates that HPRT containing cDNA are present in the selected sublibrary. The degree of enrichment as determined by densitometry is at least 500 fold.

EXAMPLE 5

Bst X1 Recognition of cDNA:RNA Hybrids

Figure 6:
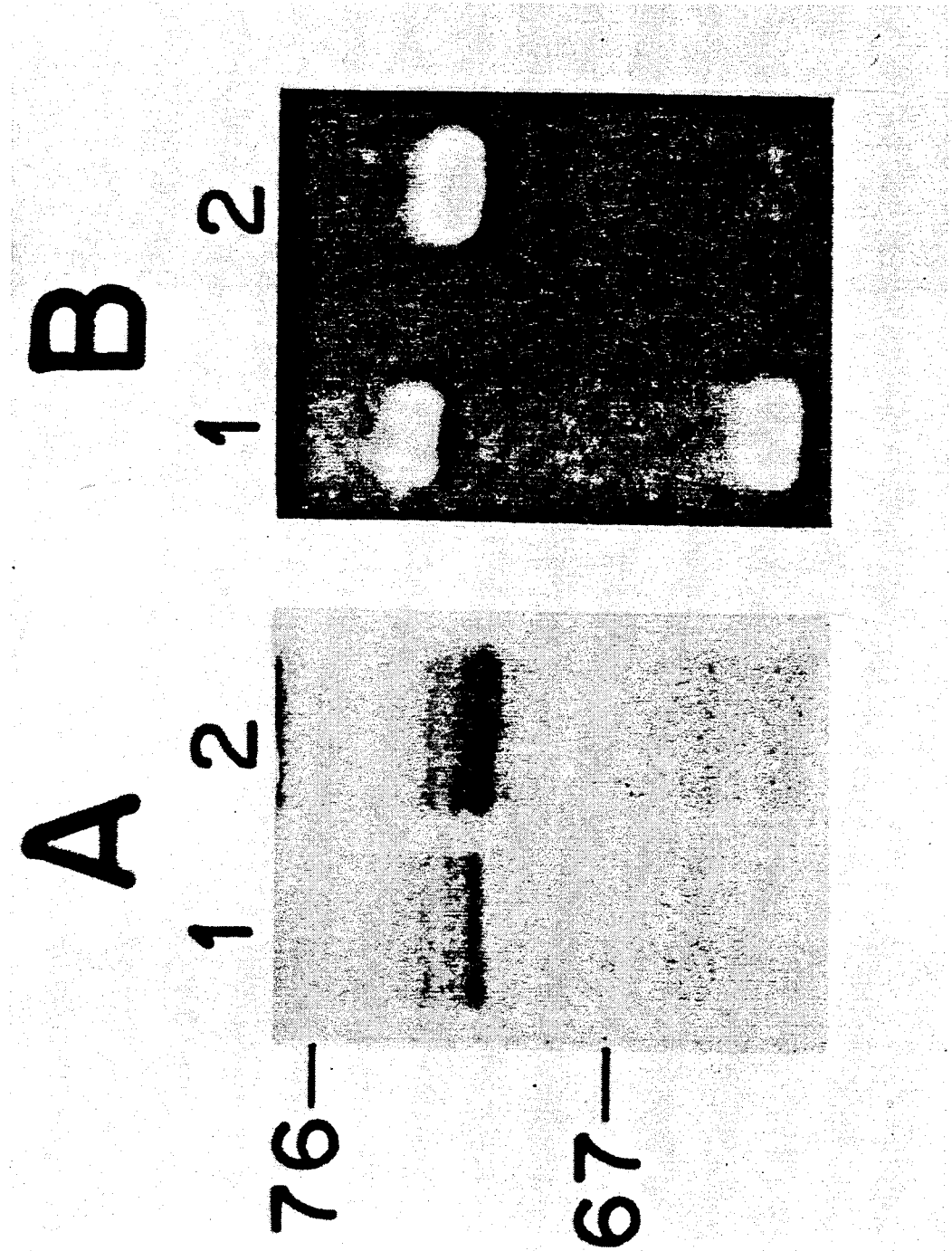
FIG. 6 is a photographic representation showing the inefficient digestion of RNA-DNA hybrids by Bst X1.

A potential problem with the use of Bst X1 to generate the oligo (dG) cohesive end is the possibility that this enzyme will recognize and cleave BSt X1 sites present in the cDNA:RNA hybrids. To test this possibility, a single stranded probe containing a Bst X1 recognition site is made by 5'$^{32}$P labeling the Hind III site present in the polylinker region of the plasmid BSB+, digesting the plasmid with Pvu II and isolating the single stranded 172 bp DNA fragment from a strand separation gel. This probe is then hybridized to a transcript, from the same plasmid, generated using T7 RNA polymerase and the DNA:RNA hybrid digested with Bst X1. To insure that digestion of only the DNA:RNA hybrids, and not unhybridized single stranded probe is assayed, the hybrids are then digested with S1 nuclease. A protected fragment of 72 bp is expected to follow S1 nuclease digestion if Bst X1 did not cleave the DNA:RNA hybrid. The results of this experiment are shown in FIG. 6A, where lane 1 shows the 72 bp protected fragment resulting S1 nuclease digestion alone and lane 2 shows the protected fragment following digestion with Bst X1 and S1 nuclease. Comparison of these bands demonstrates that little or no digestion of the RNA:DNA duplexes occurred. To assay for Bst X1 digestion of double stranded DNA, unlabeled BSB+ DNA is included in the same reactions and the extent of digestion of this template is assayed by electrophoresis on 1% (w/v) agarose gels and staining with ethidium bromide as shown in FIG. 6B. Comparison of lane 1 (no Bst X1) with lane 2 (plus Bst X1) demonstrates that, in contrast to the RNA:DNA hybrid, greater than 95% of the Bst X1 sites present in double stranded DNA are cleaved under these conditions. These results suggest that digestion of the vector:cDNA:RNA hybrid with Bst X1 does not result in cleavage within the cDNA sequences.

What is claimed is:

1. A recombinant DNA molecule comprising:
   (a) a prokaryotic origin of replication derived from pBR322;
   (b) a selectable marker;
   (c) a deoxyribonucleic acid sequence permitting synthesis of said recombinant DNA molecule in a single-stranded form; and
   (d) a unique BstXI restriction endonuclease site having the sequence 5'CCANGGGG/NTGG-3' which upon digestion with BstXI recircularizes the linear form of said recombinant molecule containing cDNA by intramolecular ligation and primes second strand synthesis.

2. A recombinant DNA molecule comprising:
   (a) a prokaryotic origin of replication;
   (b) an antibiotic resistance gene;
   (c) a deoxyribonucleic acid sequence permitting synthesis of said recombinant DNA molecule in a single-stranded form; and
   (d) a unique BstXI restriction endonuclease site having the sequence 5'CCANGGGG/NTGG-3' which upon digestion with BstXI recircularizes the linear form of said recombinant molecule containing cDNA by intramolecular ligation and primes second strand synthesis.

3. A recombinant DNA molecule comprising:
   (a) prokaryotic origin of replication;
   (b) a selectable marker;
   (c) a deoxyribonucleic acid sequence permitting synthesis of said recombinant DNA molecule in a single-stranded form wherein said sequence is the intergenic region on bacteriophage F1; and
   (d) a unique BstXI restriction endonuclease site having the sequence 5'CCANGGGG/NTGG-3' which upon digestion with BstXI recircularizes the linear form of said recombinant molecule containing cDNA by intramolecular ligation and primes second strand synthesis.

4. A recombinant DNA molecule comprising:
   (a) prokaryotic origin of replication;
   (b) a selectable marker;
   (c) a deoxyribonucleic acid sequence permitting synthesis of said recombinant DNA molecule in a single-stranded form;
   (d) a unique BstXI restriction endonuclease site having the sequence 5'CCANGGGG/NTGG-3' which upon digestion with BstXI recircularizes the linear form of said recombinant molecule containing cDNA by intramolecular ligation and primes second strand synthesis;
   (e) an eukaryotic origin of replication; and
   (f) an eukaryotic promoter.

5. The recombinant DNA molecule according to claim 2 wherein the antibiotic resistance gene encodes resistance to ampicillin.

6. A recombinant DNA molecule having the identifying characteristics of BSB+, accorded the ATCC accession number 67724.

7. A recombinant DNA molecule having the identifying characteristics of BSB−, accorded the ATCC accession number 67725.

8. The recombinant DNA molecule according to claim 4 wherein said eukaryotic origin of replication is derived from Simian Virus 40 and the eukaryotic promoter is the Simian Virus 40 early promoter.

9. The recombinant DNA molecule according to claim 4 wherein the prokaryotic origin of replication is derived from pBR322.

10. The recombinant DNA molecule according to claim 4 wherein the selectable marker is an antibiotic resistance gene.

11. The recombinant DNA molecule according to claim 10 wherein the antibiotic resistance gene encodes resistance to ampicillin.

12. The recombinant DNA molecule according to claim 4 wherein the deoxyribonucleic acid a sequence permitting synthesis of said recombinant DNA molecule in single-stranded form is the intergenic region from bacteriophage F1.

13. The recombinant DNA molecule having the identifying characteristics of pcDpoly B+, accorded the ATCC accession number 67726.

14. The recombinant DNA molecule having the identifying characteristics of pcDpoly B−, accorded the ATCC accession number 67727.

15. In a process for preparing a circular recombinant DNA molecule containing a first cDNA strand by annealing poly (A)+RNA to an oligo (dT) primer, said primer linked to a linear form of said recombinant DNA molecule; permitting synthesis of said cDNA strand, terminating said strand with oligo (dC), digesting the resulting DNA:RNA hybrid-recombinant DNA molecule complex with a restriction endonuclease that recognizes a unique site in said recombinant DNA molecule, the improvement comprising re-circularizing said complex by an intramolecular ligation between the oligo (dC) terminated cDNA strand and an oligo (dG) terminus generated by the digestion of said complex with said restriction endonuclease.

16. The process according to claim 15 wherein the unique restriction endonuclease is Bst X1.

17. A recombination DNA molecule selected form the group consisting of molecules having the identifying characteristics of BSB+, accorded the ATCC accession number 67724, BSB−, accorded the ATCC accession number 67725, pcDpoly B+, accorded the ATCC accession number 67726, and pcDpoly B−, accorded the ATCC accession number 67727; and which further comprises a first cDNA strand or a first cDNA strand and a second cDNA strand.

18. A host cell transformed with the recombinant DNA molecule of any one of claims 5, 6, 7, 8–12, 13 14, 17 and 1–14.

19. The host cell according to claim 18 wherein said host is *Escherichia coli*.

* * * * *

UNITED STATES PATENT AND TRADEMARK OFFICE
CERTIFICATE OF CORRECTION

PATENT NO. : 5,238,834
DATED : August 24, 1993
INVENTOR(S) : Steven C. Pruitt

It is certified that error appears in the above-indentified patent and that said Letters Patent is hereby corrected as shown below:

```
        Column 2, line 4:    "plasmin"  should read
--plasmid--
        Column 2, line 39:   "or"  should read --of--
        Column 3, line 9:    "hereof"  should read
--thereof--

Column 4, line 22:   after "region" insert --of--

Column 5, line 16:   "198"  should read --1983--
        Column 6, line 31:   "(1)"  should read --1)--
        Column 8, line 68:   "lib aries"  should read
--libraries--
        Column 9, line 28:   "2X10⁵"  should read
--2X10⁻⁵--
```

Column 9, line 28: "$2 \times 10^5$" should read --$2 \times 10^{-5}$--

UNITED STATES PATENT AND TRADEMARK OFFICE
CERTIFICATE OF CORRECTION

PATENT NO. : 5,238,834
DATED : August 24, 1993
INVENTOR(S) : Steven C. Pruitt

It is certified that error appears in the above-indentified patent and that said Letters Patent is hereby corrected as shown below:

Column 9, line 32: "HPRT+" should read --$HPRT^{+}$--
Column 10, line 28: "$10^7$" should read --$10^{-7}$--
Column 10, line 36: "OIAI" should read --O1A1--
Column 10, line 40: "$10^7$" should read --$10^{-7}$--
Column 11, line 68: "$CHCl_1$" should read --$CHCl_3$--

Column 15, line 26: "+his" should read --this--
Column 16, line 66: after "hours" insert --.--
Column 17, line 8: after "obtained" insert --.--
Column 19, line 13, Claim 12: after "acid" delete --a--
Column 20, line 12, Claim 17: "form" should read --from--

Signed and Sealed this

Seventh Day of June, 1994

BRUCE LEHMAN

*Attest:*

*Attesting Officer*     *Commissioner of Patents and Trademarks*